(12) United States Patent
Landry et al.

(10) Patent No.: US 7,348,403 B2
(45) Date of Patent: Mar. 25, 2008

(54) PEPTIDES AND METHODS FOR DEACTIVATION OF ORGANOPHOSPHORUS-BASED NERVE AGENTS AND INSECTICIDES

(75) Inventors: Donald W. Landry, New York, NY (US); Shi-Xian Deng, White Plains, NY (US)

(73) Assignee: The Trustees of Columbia University in the City of New York, New York, NY (US)

( * ) Notice: Subject to any disclaimer, the term of this patent is extended or adjusted under 35 U.S.C. 154(b) by 0 days.

(21) Appl. No.: 10/538,310

(22) PCT Filed: Dec. 8, 2003

(86) PCT No.: PCT/US03/39207

§ 371 (c)(1),
(2), (4) Date: Apr. 13, 2006

(87) PCT Pub. No.: WO2004/052918

PCT Pub. Date: Jun. 24, 2004

(65) Prior Publication Data

US 2006/0216778 A1 Sep. 28, 2006

Related U.S. Application Data

(60) Provisional application No. 60/431,897, filed on Dec. 9, 2002.

(51) Int. Cl.
*A61K 38/00* (2006.01)
*C07K 5/00* (2006.01)
*C07K 6/00* (2006.01)
*C07K 16/00* (2006.01)
*C07K 17/00* (2006.01)

(52) U.S. Cl. ............................................ 530/329; 514/2
(58) Field of Classification Search ................ 530/329; 514/2
See application file for complete search history.

(56) References Cited

U.S. PATENT DOCUMENTS

| | | | |
|---|---|---|---|
| 4,312,946 A | | 1/1982 | Wood et al. |
| 5,432,018 A | * | 7/1995 | Dower et al. ................. 435/6 |
| 5,843,758 A | | 12/1998 | Russell et al. |
| 5,928,927 A | | 7/1999 | Cheng et al. |
| 5,948,658 A | * | 9/1999 | Landry ..................... 435/188.5 |
| 6,080,566 A | | 6/2000 | Cheng et al. |

FOREIGN PATENT DOCUMENTS

| | | |
|---|---|---|
| WO | WO 99/16417 | 4/1999 |
| WO | WO 00/48684 | 8/2000 |
| WO | WO 00/49363 | 8/2000 |
| WO | WO 00/51687 | 9/2000 |
| WO | WO 01/85318 A2 | 11/2001 |

OTHER PUBLICATIONS

Cho et al. Applied and Environment Microbiology 2002;68(4):2026-2030.*
Stewart et al., "A Model for the Mechanism of Human Topoisomerase I," Science, 1998, 279, 1534-41.*
New England Biolabs Catalog, 1998/99, pp. 140-1.*
International Search Report issued by the International Searching Authority issued Apr. 4, 2005 in connection with related International Application No. PCT/US2003/039207.
Cho, C. M.-H., Mulchandani, A., and Chan, W. (2002). Bacterial Cell Surface Display of Organophosphorus Hydrolase for Selective Screening of Improved Hydrolysis of Organophosphate Nerve Agents. *Appl. Environ. Microbial.* 68: 2026-2030.
Cheng, T.-C., Harvey S. P., and Chen, G. L. (1996), Cloning and Expression of a Gene Encoding a Bacterial Enzyme for Decontamination of Organophosphorus Nerve Agents and Nucleotide Sequence of the Enzyme. *Appl. Environ. Microbiol.* 62: 1636-1641.
Gill, I. and Ballensteros, A. (2000) . Degradation of Organophosphorus Nerve Agents by Enzyme-Polymer Nanocomposites: Efficient Biocatalytic Materials for Personal Protection and Large-Scale Detoxification. *Biotechnol. Bioeng.* 70: 400-410.
LeJeune, K. E. and Russell, A. J. (1999). Biocatalytic Nerve Agents Detoxification in Fire Fighting Foams. *Biotechnol. Bioeng.* 62: 659-665.
LeJeune, K. E., Wild, J. R., and Russell, A. J. (1998). Biocatalytic Nerve Agents Detoxification in Fire Fighting Foams. *Nature* 395:27-28.
LeJeune; K. E., Dravis, B. C., Yang, F., Hetro, A. D., Doctor, B. P., and Russell, A. J. (1998). Fighting Nerve Chemical Weapons with Enzyme Technology: *Ann. N.Y. Acad. Sci.* 864: 153-170.

* cited by examiner

*Primary Examiner*—Cecilia J. Tsang
*Assistant Examiner*—Maury Audet
(74) *Attorney, Agent, or Firm*—John P. White; Cooper & Dunham LLP

(57) ABSTRACT

This invention provides methods and peptides for the inactivation of organophosphorus-based insecticides and chemical warfare agents. The instant methods include peptide screening methods, peptides and peptide libraries, related compositions of matter, articles of manufacture, and methods for prophylaxis, treatment, decontamination and detection.

7 Claims, 5 Drawing Sheets

Scheme 3

PEPTIDES AND METHODS FOR DEACTIVATION OF ORGANOPHOSPHORUS-BASED NERVE AGENTS AND INSECTICIDES

This application is a §371 national stage of PCT International Application No. PCT/US2003/039207, filed Dec. 8, 2003, and claims the benefit of U.S. Provisional Application No. 60/431,897, filed Dec. 9, 2002, the contents of which are hereby incorporated by reference.

The invention disclosed herein was made with United States government support under grant numbers TLN 10-122 and DO 0788 from the Department of the Army, Army Research Office 1132; Scientific Services Program. Accordingly, the United States government has certain rights in this invention.

Throughout this application, various publications are referenced by author and date. Full citations for these publications may be found at the end of the specification immediately preceding the claims. The disclosures of these references in their entireties are hereby incorporated by reference into this application to describe more fully the art to which this invention pertains.

BACKGROUND OF THE INVENTION

Irreversible inhibitors of acetylcholinesterase (AChE) are used extensively as insecticides and have also been used as chemical weapons. World-wide stockpiles of these agents for use in chemical warfare are estimated to exceed 200,000 tons (Lejeune et al, 1998). The extreme toxicity of these compounds and their global proliferation has made the development of protective agents and antidotes an important research priority.

AChE inhibitors are derivatives of phosphoric, pyrophosphoric and phosphonic acids. These agents react to form a phosphoester with the serine residue that resides in the active site of the AChE enzyme. This phosphoester form of the enzyme is inactive, although the active enzyme can be regenerated through hydrolysis of the phosphoester.

The toxicity of the organophosphorus agents arises from the stability of the phosphoester intermediate that is formed with the enzyme. As its name implies, AChE functions to cleave the ester linkage of acetylcholine, forming acetic acid and choline. To do this, the enzyme transiently forms an ester with the carboxyl moiety of acetylcholine, releasing choline. The resulting carboxylate ester of the enzyme is inactive. However, this ester undergoes rapid hydrolysis, measured in milliseconds, to regenerate the original, active form of the enzyme. In contrast, the rates of hydrolysis for the phosphate esters of AChE are measured in hours. The reversible inhibitors of AChE that are used clinically generate a carbamylated enzyme and have rates of hydrolysis measured in minutes. Thus, the time required for regeneration of the active enzyme via hydrolysis of the ester linkage of the inactive, acetylated enzyme defines the difference between the enzyme's normal function, reversible inhibition, and irreversible inhibition.

One strategy for developing antidotes to irreversible AChE inhibitors has been the synthesis of highly nucleophilic small molecules capable of efficiently cleaving phosphate esters. Hydroxylamine is one such compound that was demonstrated to significantly increase the rate of hydrolysis of phosphorylated AChE. However, efficient hydrolysis was only achieved at toxic concentrations of hydroxylamine.

To date, this approach has yielded only one compound that has shown clinical efficacy, 2-pyridine aldoxime methylchloride (2-PAM). The oxygen atom of this molecule is part of an oxime functional group. The oxime moiety is a hydroxylamine-like nucleophile formed from the reaction of hydroxylamine with aldehydes or ketones. The effectiveness of this compound is limited by its inability to cross the blood-brain barrier. However, effectiveness is further impaired by an inability to regenerate the enzyme once "aging" has occurred. This latter impediment means that treatment is only effective if administered within a few minutes to a few hours of toxin exposure, depending on the toxin.

Organophosphorus agents, particularly some of the more recent additions to chemical weapons arsenals, have the propensity to become truly irreversible inhibitors through the aging process. This molecular process occurs when, having first reacted with AChE to inactivate the enzyme, a phosphoester bond undergoes cleavage, resulting in an anionic ester which is extremely resistant to hydrolysis. The phosphorylated enzyme which has aged in this way is completely refractory to regeneration by currently available antidotal agents, including 2-PAM. It is this aging process that makes the phosphorus-derived chemical warfare agents, such as sarin, soman, VX and tabun, extremely lethal.

In addition to efforts to produce antidotes, research has focused on protecting against exposure to organophosphorus agents, thereby preventing or moderating their toxic effects. One important strategy has been the use of recombinant enzymes for the biocatalytic degradation of organophosphorus agents. This methodology is being utilized in the development of protective clothing as well as agents for surface or aerial decontamination. In these methodologies, microbial enzymes, such as cholinesterases or organophosphorus hydrolases, are attached to a solid support in a manner that retains some portion of their catalytic activity. Such biocatalytic materials include silicone polymers (Gill 2000) and polyurethane foams (LeJeune 1996, 1999; Cheng 1996).

Peripheral blocking methods, i.e., methods that rely on agents that would intercept nerve agents in the circulatory system before they partition into the central nervous system or muscle, are currently the only choice for protection against organophosphorus agents. The standard technology in use today for protection against nerve agents is based upon the recombinant enzyme, butyrylcholinesterase (BuChE). BuChE rapidly reacts with nerve agents to form an intermediate phosphoester with a serine in the active site much as occurs when these agents react with AChE. Compounding the slow rate of hydrolysis of this intermediate is the inactivation of the enzyme through the process of molecular aging discussed above. Thus, BuChE is essentially an autocatalytic stoichoeometric blocker rather than a true hydrolytic enzyme. Butyrylcholinesterase mutants demonstrate enzymatic turnover, but low turnover, combined with high immunogenicity, an inability to cross the blood-brain barrier and a high equivalent weight ratio (almost 500:1 for butyrylcholinesterase to nerve gas). These factors make it difficult to maintain in vivo enzyme levels sufficient to protect against a lethal dose of a toxin such as a nerve agent.

To date, the above-mentioned shortcomings have not been overcome.

SUMMARY OF THE INVENTION

This invention provides a method for determining whether a peptide forms a phosphorus based ester with an organophosphorus agent. This invention also provides a method for determining whether, among a plurality of peptides, there exists a peptide that forms a phosphorus-based ester with an organophosphorus agent. This invention further provides a method for identifying and characterizing a peptide, among a plurality of peptides, that forms a phosphorus-based ester with an organophosphorus agent. This invention further provides a peptide which forms a phosphorus-based ester with an organophosphorus agent, which peptide comprises a nucleophilic functional group. This invention also provides a peptide library, wherein each peptide therein comprises a nucleophilic functional group. This invention further provides a composition of matter comprising a peptide and a pharmaceutical or a nonpharmaceutical carrier. This invention also provides an article of manufacture comprising a peptide affixed to a solid substrate.

This invention, further provides a method for reducing the likelihood, of injury due to exposure to an organophosphorus-containing agent in a subject exposed to or at risk of exposure to such agent, comprising administering to the subject an effective amount of a peptide of the instant invention.

This invention also provides a method for decontaminating an area exposed to an organophosphorus-containing agent comprising introducing to the area an effective amount of a peptide of the instant invention. This invention further provides a kit for decontaminating an area exposed to an organophosphorus-containing agent comprising the instant peptides and instructions for use.

Finally, this invention provides a method for determining the presence of an organophosphorus-containing agent in an area.

DETAILED DESCRIPTION OF THE INVENTION

Definitions

Figure 1:
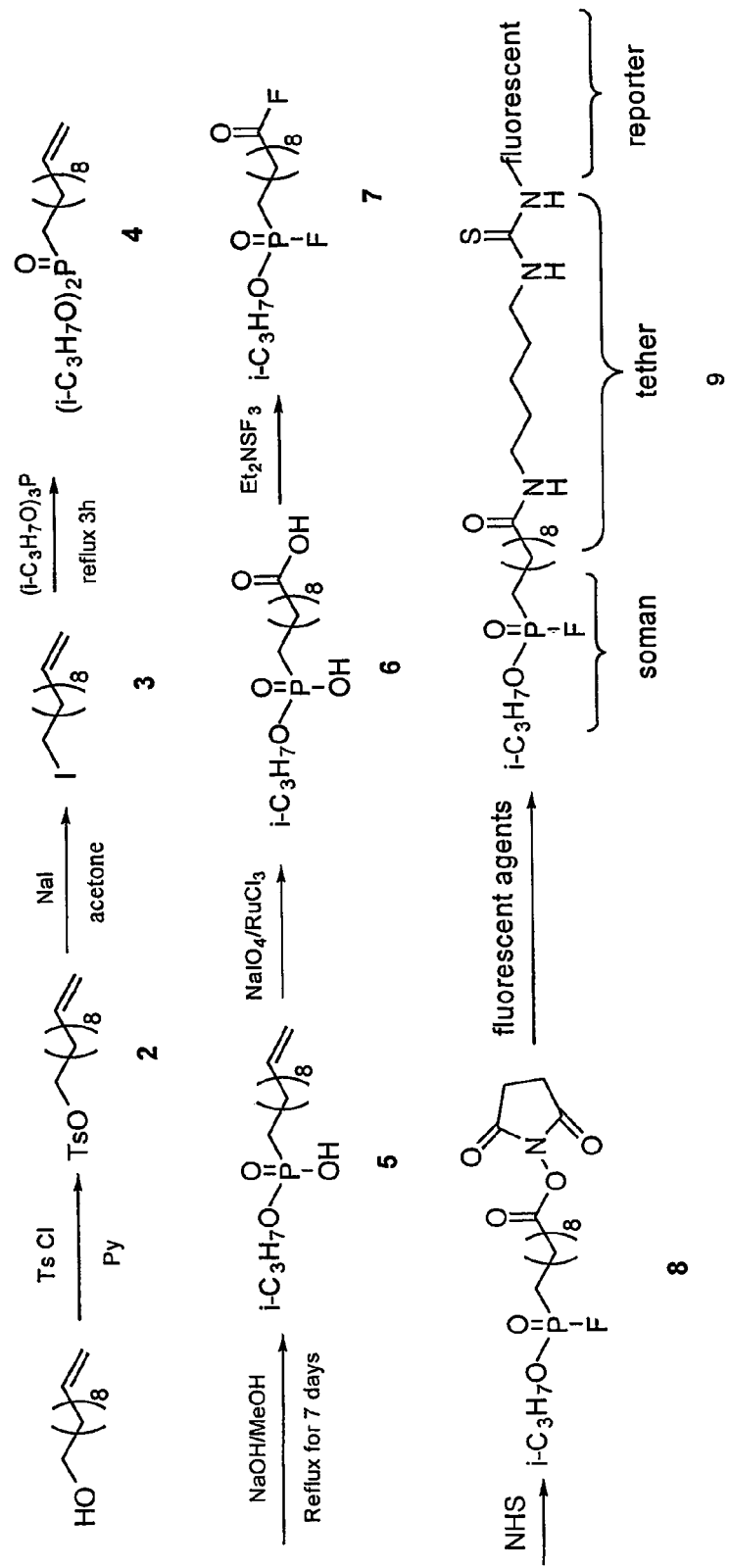
FIG. 1: A sarin analog tethered to a fluorescent label was synthesized as shown to provide a low toxicity version of soman that would retain its chemical reactivity and report its reaction with a peptide molecule displayed on a library bead.

In this invention, "administering" can be effected or performed using any of the various methods and delivery systems known to those skilled in the art. The administering can be performed, for example, intravenously, orally, via implant, transmucosally, transdermally, intramuscularly, and subcutaneously. In a preferred embodiment, the peptide is administered intramuscularly.

Determining an "effective amount" of the instant peptide for decontamination purposes can be done based on in vitro data. Determining an effective amount of the instant peptide for administering to a subject can be done based on animal data using routine computational methods. In one embodiment, the effective amount contains between about 10 mg and 1000 mg of the instant peptide. In another embodiment, the effective amount contains between about 50 mg and about 500 mg of the peptide. In a further embodiment, the effective amount contains between about 100 mg and about 250 mg of the peptide, and preferably about 200 mg thereof.

"Pharmaceutical carriers" are well known in the art and include, but are not limited to, 0.01-0.1 molar phosphate buffer, 0.8% saline solution, propylene glycol, polyethylene glycol, vegetable oils and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's or fixed oils. Intravenous vehicles include fluid and nutrient replenishers, electrolyte replenishers such as those based on Ringer's dextrose, and the like. Preservatives and other additives may also be present, such as, for example, antimicrobials, antioxidants, chelating agents, inert gases and the like.

"Nonpharmaceutical carriers" include, without limitation, foams and aerosols. For example, a polyurethane foam can be synthesized to incorporate a peptide of the instant invention using methods standard in the art of polymer synthesis. In one example, a hydrophilic polyurethane prepolymer is reacted with water containing the peptide and a surfactant, forming a foam. Such prepolymers are known in the art and comprise a urethane capped with multiple isocyanate functionalities. As one of skill in the art would be aware, various surfactants can be used in order to alter the porosity, density and surface properties of the foam.

The term "organophosphorus agent" is synonymous with "organophosphorus-based agent", and is used herein to refer to a chemical compound comprising carbon, hydrogen, phosphorous and oxygen. Organophosphorus agents include, without limitation, phosphorus-based esters. A number of commercially important insecticides, as well as chemical warfare agents, contain a phosphorus-based -ester moiety which either is inherently toxic to humans or is readily converted into a toxic moiety. Examples of such agents include, without limitation, malathion, parathion, paraoxon, schradan, dichlorfenthion, soman, sarin, VX, GB and tabun.

The term "phophorus-based ester" is used herein to refer to any ester of phosphorous. Examples of such esters include, without limitation, a phosphate ester, a phosphonate ester and a phosphinate ester.

The term "peptide" is used herein to refer to a polymer of amino acid residues. In one embodiment, a peptide has 15 or fewer amino acid residues. Amino acid residues include, without limitation, any of the 20 naturally occurring amino acids or modifications thereof, as well as natural or synthetic derivatives thereof. A peptide can also comprise one or more modified amino acid residues. Modifications include, without limitation, the conjugation to, an amino acid residue of a non-protein moiety (e.g. an oxime or a cyclodextran). Other modifications include the addition of a chemical tag useful for identification or purification. Examples of chemical tags include, without limitation, a biotin molecule a radioisotope and a fluorescent molecule.

As used herein, a "solid substrate" and a "solid support" are synonymous, and shall mean any water- and/or lipid-insoluble support to which a peptide can be affixed. Examples of solid supports include, without limitation, alumina pellets, trityl agarose and glass/silica beads, and polymers such as nylons, acrylates, and silicas.

"Subject" shall mean any animal, such as a primate, mouse, rat, guinea pig or rabbit. In the preferred embodiment, the subject is a human Embodiments of the Invention This invention provides a method for determining whether a peptide forms a phosphorus-based ester with an organophosphorus agent comprising the steps of contacting the peptide with the agent under conditions permitting the formation of a phosphorus-based ester and determining whether a phosphorus-based ester has formed.

This invention also provides a method for determining whether, among a plurality of peptides, there exists a peptide that forms a phosphorus-based ester with an organophosphorus agent. This method comprises the steps of contacting the plurality of peptides with the agent under conditions permitting formation of a phosphorus-based ester and determining whether a phosphorus-based ester has, formed.

This invention further provides a method for identifying and characterizing a peptide among a plurality of peptides that forms a phosphorus-based ester with an organophosphorus agent. This method comprises the steps of contacting the agent with the plurality of peptides under conditions permitting the formation of a phosphorus-based ester, identifying the peptide or peptides that form such an ester with the agent and determining the amino acid sequence of the peptide so identified.

In an embodiment of any of these methods, the organophosphorus agent which reacts with a peptide is selected from the group consisting of malathion, parathion, paraoxon, schradan, dicholorfenthion, soman, sarin, VX, GB and tabun, or an analog thereof.

In any of these three methods, the phosphorus-based ester can be any ester of phosphorus including, for example, a phosphate ester, a phosphonate ester or a phosphinate ester.

Figure 2:
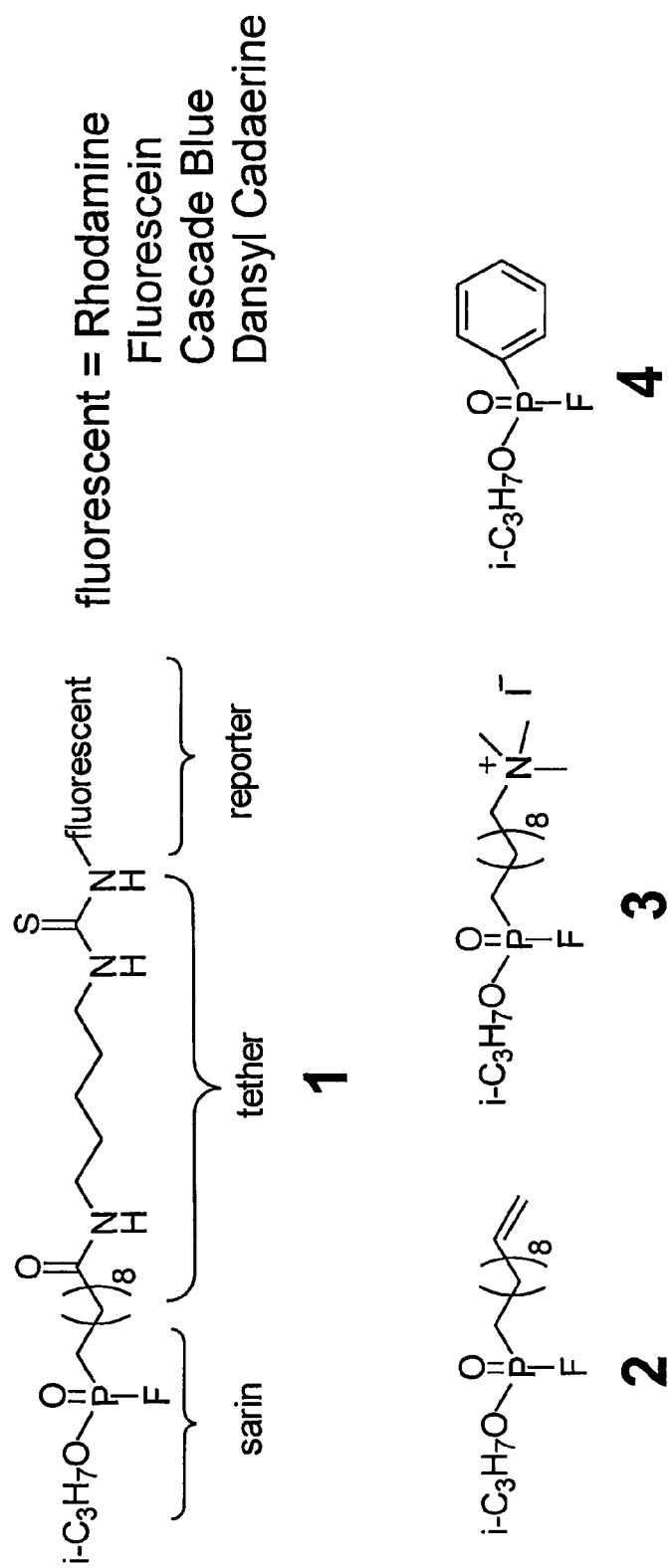
FIG. 2: Structure of the fluorescently labeled sarin analog (1) and additional analogs with the following properties, hydrophobicity (2), water-solubility (3) and UV-activity (4).

In one embodiment of the instant methods, the peptides are bound to a solid support such as a bead, a microtiterplate, a glass chip or a silicone chip. In another embodiment, the agent is labeled with a detectable marker. In a preferred embodiment, the detectable marker is a radioisotope, a fluorescent molecule, biotin or an enzyme. In one example, the agent is a nerve agent and the detectable marker is rhodamine. In another example, the agent has the structure set forth as analog (1) in FIG. 2, which is a rhodamine-conjugated analog of the nerve agent soman.

In another embodiment of the instant methods, the peptides are not bound to a solid support. Instead, the agent or peptide is labeled with a moiety that provides a basis for affinity purification. Such moieties are well-known in the art and include, for example, biotin and glutathione. Such purification can comprise a step of removing unreacted peptide and agent prior to affinity purification. This step may be accomplished in a number of ways using techniques that are well-known in the art, such as chemical separation based on solubility, size exclusion chromatography and gel electrophoresis.

This invention also provides a peptide which forms a phosphorus-based ester with an organophosphorus agent, which peptide comprises a nucleophilic functional group. In one embodiment of this invention, the nucleophilic functional group comprises a thiol or a hydroxyl group. In a preferred embodiment, the peptide is between six and 15 amino acids in length or has a molecular weight of less than 1500 daltons. In one embodiment, the peptide is six amino acids in length.

In the preferred embodiment of this invention, the agent with which the peptide reacts is an organophosphorus insecticide or chemical warfare agent.

This invention also provides a peptide library, wherein each peptide therein comprises a nucleophilic functional group. In one embodiment, each peptide in the library comprises a thiol or hydroxyl-containing amino acid residue, and the position at which such thiol or hydroxyl-containing amino acid residue occurs is the same for each peptide in the library. In another embodiment, each peptide is of a fixed length. In a further embodiment, the length of each peptide is between six and 15 amino acid residues and/or the molecular weight of each peptide is less than 1500 daltons. In a further embodiment, each peptide has a length of six amino acid residues. In still another embodiment, the first, second, third, fourth, fifth, or sixth amino acid residue in each hexapeptide is a serine.

This invention also provides a composition of matter comprising one of the instant peptides and a pharmaceutical carrier. This invention further provides a composition of matter comprising one of the instant peptides and a nonpharmaceutical carrier. In one embodiment, the nonpharmaceutical carrier is a foam or aerosol.

Foam formulations and mechanisms for their dispersal are well-known in the art and are particularly useful for surface decontamination. Foam formulations specifically designed for blast suppression are also known in the art and would be particularly useful in combination with the peptides of the instant invention in containing an explosive device that has been designed to disseminate a nerve agent.

This invention also provides an article of manufacture comprising one of the instant peptides affixed to a solid substrate. In one embodiment, the solid substrate is a polymer. In another embodiment, the solid substrate is a fabric or fiber. In yet another embodiment, the solid substrate is a filtration component, such as one used in a gas mask.

In the preferred embodiment, the peptides of the instant invention are incorporated into polymers using art-recognized techniques. Many different types of polymers are known in the art. The choice of polymer would depend, for example, upon whether the peptide is to be incorporated into protective clothing, a device such as a gas mask or a pellet or sheet for surface decontamination.

This invention provides a method for reducing the likelihood of injury due to exposure to an organophosphorus agent in a subject exposed to or at risk of exposure to such an agent. This method comprises administering to the subject an effective amount of a peptide of the instant invention.

This invention also provides a method for decontaminating an area exposed to an organophosphorus agent comprising introducing to the area an effective amount of a peptide of the instant invention.

This invention further provides a kit for decontaminating an area exposed to an organophosphorus agent comprising a peptide of the instant invention and instructions for use.

Finally, this invention provides a method for determining the presence of an organophosphorus agent in an area. This method comprises the steps of contacting a peptide of the instant invention with a sample taken from the area and determining whether a phosphorus-based ester is formed with the peptide. In this method, the formation of such an ester is indicative of the presence of an organophosphorus agent in the area.

This invention is illustrated in the Experimental Details section which follows. This section is set forth to aid in an understanding of the invention but is not intended to, and should not be construed to, limit in any way the invention as set forth in the claims which follow thereafter.

Experimental Details

Synopsis

The present invention provides methods and reagents for protection against poisoning by organophosphorus-based insecticides and nerve agents. In a novel approach to producing such reagents, this invention utilizes combinatorial chemistry and high-throughput screening to generate catalytic peptides for the inactivation of organophosphorus-based toxins. The peptides provided by the instant invention are selected based on their ability to autocatalytically bind and thereby inactivate substrate phosphoesters and offer several advantages over current enzyme-based approaches. These include decreased immunogenicity, and more favorable equivalent weight ratios.

Methods

Design of the Peptide Library

A combinatorial approach based on "split and pool" synthesis was used to generate a diverse population of peptides. Hexapeptide libraries were designed with five random positions and one fixed serine, giving 3.2 million unique peptides per library. Separate libraries were generated that contained a serine at each position, $[x_1, x_2 \ldots x_6]$ in the peptide. Thus, a total of six libraries is produced, each having serine fixed in a different position of the hexapeptide.

Synthesis of the Peptide Libraries

Tental Gel™ was used as the solid phase support and sequences of active peptides were determined using mass spectrometry (MS). Peptide library synthesis was accomplished by a "split and pool" methodology using standard Fmoc peptide chemistry. For example, the first library, in which serine occupies the first position, $x_1$, was synthesized as follows: (i) the beads were reacted with Fmoc-protected serine using benzotriazol-1-yloxytris (dimethylamino) phosphonium hexafluorophosphate (BQP) and hydroxybenzotriazole (HoBt) as coupling agents, (ii) amino groups were blocked with acetic anhydride, and (iii) the Fmoc protecting group was removed using 20% piperidine in DMF. The next five amino acids in the peptide were placed randomly using the "split and pool" method. This is accomplished by separating the entire population of beads into twenty groups of equal size. Each of the twenty amino acids is reacted with an individual group using BOP and HoBt as coupling agents. After the coupling reaction, the beads are combined so that they can be washed, blocked, and finally deprotected together. This split and pool synthesis is performed five times in order to add five random amino acids to each peptide.

Library Screening

Libraries were exposed to a fluorescently labeled nerve gas analog for 1 hr followed by 1 minute washes at room temperature in PBS containing 10% Tween 20, 10% DMF, followed by DMF containing 10% Tween 20. Butylcholinesterase coupled to native beads was used as a positive control. Library peptides which remained fully protected and thus unreactive were used as a negative control. Wash conditions were optimized to exclude noncovalent interactions between the fluorescent label and the beads utilizing either peptides in which the reactive groups were blocked by pre-incubation with either acetic anhydride or a single "non-specific" peptide not likely not to be configured for reaction.

Following incubation with analog (1) and extensive washing, beads displaying relatively high levels of fluorescence were selected and their peptides sequenced using LCMS. Peptides corresponding to those identified in the screen were synthesized using Tental Gel™ as the solid phase and standard Fmoc chemistry, then purified using high-pressure liquid chromatography (HPLC).

Synthesis of Fluorescent Sarin Analogs

Fluorescent-labeled sarin analogs were synthesized as shown in FIG. 1. Briefly, 10-undecen-1-ol (1) was converted to an iodinated compound (3) through a tosylate intermediate (2). Reaction of (3) with excess tri-isopropylphosphite under reflux conditions afforded the di-isopropoxy phosphonate (4), which was converted to the isopropoxyhydroxy phosphonate (5) by refluxing with NaOH in methanol. The olefin (5) was oxidatively cleaved with ruthenium trichloride and sodium periodate to yield the terminal carboxylic acid (6). Treatment of (6) with excess diethylaminosulfur trifluoride (DAST), followed by N-hydroxysuccinimide (NHS), afforded the N-succinyl fluorophosphonate intermediate (8) Without further purification compound (8) was reacted with amine-functionalized rhodamine ($NH_2$-rhodamine) to generate the rhodamine-labeled sarin analog (9). The structures of the compounds 2-8 and 9 (analog 1) were determined by NMR and MS. Experimental details are set forth below.

Compound (2) [1-((p-toluenesulfonyl)oxy)-10-undecene]: A solution of (1) (5 g, 0.029 mol) in pyridine (50 ml) was reacted with p-toluenesulfonyl chloride (8.2 g, 0.044 mol) at room temperature for 4 h. The reaction mixture was evaporated and the residue was dissolved in ethyl acetate. The acetate solution was washed with 1N HCl (2×30 ml) and concentrated under reduced pressure. The product (2) was purified by chromatography ($SiO_2$, ethyl acetate/hexane 1/20). Colorless oil, yield 8.9 g, 94%, $^1H$ NMR ($CDCl_3$, 300 MHz): 7.7(d, 2H), 7.32(d, 2H), 5.8(m, 1H), 5.0(m, 2H), 4.0(t, 2H), 2.4(s, 3H), 2.0(m, 2H), 1.7(m, 2H), 1.5-1.2(m, 12H); MS: found 324.18, cald. 324.18 for $C_{18}H_{28}O_3S$.

Compound (3) [1-iodo-10-undecene]: A solution of (2) (8.0 g, 0.025 mol) in acetone (80 ml) was treated with NaI (7.0 g, 0.05 mol). The reaction mixture was refluxed for 2 h and concentrated. The residue was dissolved in ethyl acetate (50 ml) and washed with $H_2O$ (20 ml). The product (3) was purified by chromatography ($SiO_2$, ethyl acetate/hexane 1/20). 5.5 g oil, 79%. $^1H$ NMR ($CDCl_3$, 300 MHz): 5.8 (m, 1H), 5.0(m, 2H), 3.2(t, 2H), 2.0(m, 2H), 1.8 (m, 2H), 1.50-1.20(m, 12H). MS: found 280.07, cald. 280.07 for $C_{11}H_{21}I$.

Compound (4) [1-(di-isopropoxy) phosphinyl)-10-undecene]: A mixture of triisopropyl phosphite (10 ml, excess) and compound (3) (5.0 g) was refluxed for 15 h. Excess of triisopropyl phosphite was removed by distillation under reduced pressure. The product was purified by chromatography ($SiO_2$, ethyl acetate/hexane 1/4). Oil, 5.4 g, 93%. $^1H$ NMR ($CDCl_3$, 300 MHz) 5.70 (m, 1H), 4.9 (m, 2H), 4.80 (m, 2H, CHOP), 2.0-1.0 (m, 30H). MS: found 318.380, cald. 318.380 for $C_{17}H_{35}O_3P$.

Compound (5) [1-(isopropylhydroxyphosphinyl)-10-undecene]: A solution of compound (4) (5.0 g, 0.016 mol) in methanol (80 ml) and aqueous NaOH (5.0 g in 15 ml $H_2O$) was refluxed for 5 h. The solvents were removed by concentration under reduced pressure. The residue was dissolved in $H_2O$ (30 ml) and extractated with ethyl ether. The aqueous solution was acidified with 6 N HCl to pH=2, and extracted with ethyl acetate. The organic phase was evaporated to give pure compound (5) as clear oil. 3.9 g, 89%. $^1H$ NMR ($CDCl_3$, 300 MHz) 5.70 (m, 1H), 4.9 (m, 2H), 4.80(m, 1H, CHOP), 2.0-1.0 (m, 24H)

Compound (6) [10-(iso-propylhydroxyphosphinyl) decanoic acid]: To compound (5) (~1.0 g, 3.6 mmol) dissolved in $CCl_4$—$CH_3CN$—$H_2O$ (1:1:1.5) (35 ml) was added $NaIO_4$ (3.1 g, 4 eq.) and ruthenium trichloride hydrate (20 mg). The reaction mixture was stirred for 2 h at room temperature and then partitioned between $CH_2Cl_2$ (40 ml) and 1N HCl (20 ml). The organic layer was concentrated under reduced pressure and the resulting residue was purified by chromatography to give semisolid product ($SiO_2$, ethyl acetate/methanol 1/2). 0.7 g, 70%. $^1H$ NMR ($CDCl_3$) 4.70 (m, 1H, CHOP), 2.3 (t, 2H), 2.0-1.0 (m, 24H). High resolution MS: found 295.166, cald. 295.166 for $C_{13}H_{28}O_5P$.

Compound (9) [Rhodamine-labeled sarin analog (1)]: A solution of (6) (100 mg, 0.34 mmol), in $CH_2Cl_2$ (3 ml) was treated at −78° C. with diethylaminosulfur trifluoride (DAST, 0.1 mL, 0.5 mmol), and the reaction mixture was stirred for 10 min. The resulting difluoride (7) was treated in situ with, N-hydroxysuucinimide (0.4 mmol) in DMF (0.2 ml) and stirred for another 5 minutes at room temperature. The reaction mixture was partitioned between ethyl acetate (15 ml) and water (10 ml), and the organic layer was washed with brine (5 ml), dried with $Na_2SO_4$ and concentrated under reduced pressure to afford the N-hydroxysuccinimide (8). Without further purification, this compound was treated with amine-functionalized rhodamine derivative (1.0 eq) in DMF (2 ml) and stirred for 20 minutes. The solvents were evaporated under reduced pressure. The remaining residue was washed sequentially with diethyl ether and ethyl acetate to afford (9) as a red film. 150 mg, 49%, $^1H$ NMR ($CDCl_3$, 300 MHz) 7.0-8.0 (m, 9H), 4.90 (m, 1H, CHOP), 2.5-1.0 (m, 46H). High resolution MS: found 793.4105, cald. 793.4400 for $C_{43}FH_{59}N_4O_7P$.

Synthesis of Additional Sarin Analogs

Figure 3A:
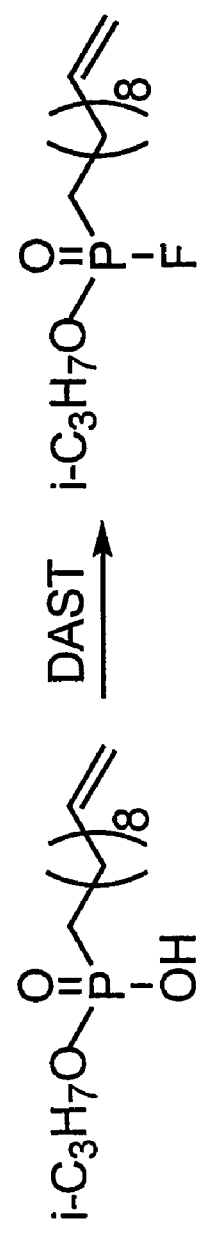
FIG. 3A: Analog (2) was synthesized by fluoration of 1-(isopropylhydroxyphosphinyl)-10-undecene with DAST.

Synthesis of analog (2): Analog (2) was synthesized by fluoration of compound (5) (FIG. 1), 1-(isopropylhydroxyphosphinyl)-10-undecene, with DAST in a similar manner to that of analog (1) shown in FIG. 1 and described above. The synthetic scheme of analog (2) is summarized in FIG. 3A.

Figure 3B:
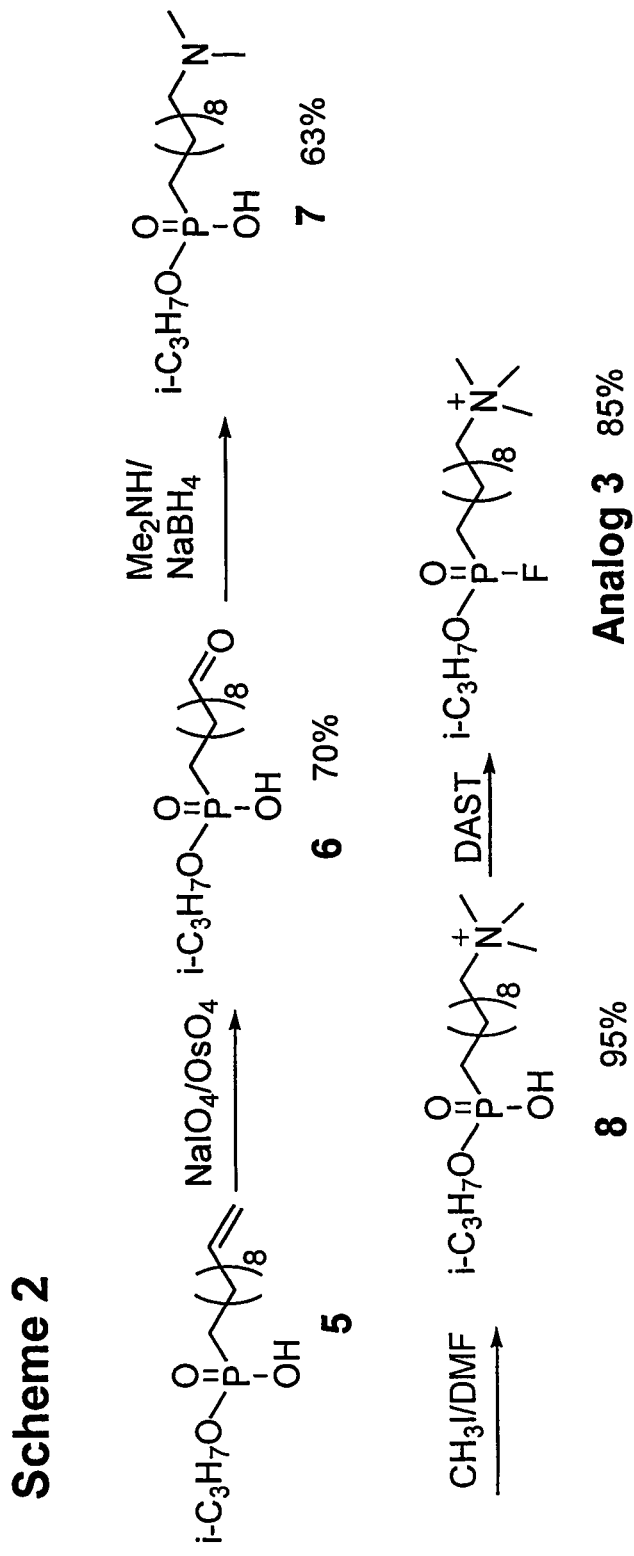
FIG. 3B: Synthesis of analog (3). The olefin (5) was oxidatively converted to aldehyde (6) with $OSO_4$ and $NaIO_4$. Reductive amination of (6) with dimethyl amine and sodium borohydride afford the amine (7). Quaternazation of the tertiary amine (7) with iodomethane in DMF gave (8) which was treated with DAST to afford the analog (3).

Synthesis of analog (3): Analog (3) was synthesized by the route outlined in Scheme 2, FIG. 3B. The olefin (5) was oxidatively converted to an aldehyde (6) with $OsO_4$ and $NaIO_4$. Reductive amination of (6) with dimethyl amine and sodium borohydride afforded the amine (7). Quaternazation of the tertiary amine (7) with iodomethane in DMF gave (8) which was treated with DAST to afford the analog (3).

Experimental details for analog (3): Compound (5) (0.74 g) in a solution of THF (10 ml) $H_2O$ (6 ml) was added to 2% $OsO_4$ in $H_2O$ (2 ml) and $NaIO_4$ (2.0 g, 4 eq.). The mixture was stirred at room temperature for 18 h, quenched with saturated $Na_2SO_3$ (10 ml) and partitioned with ethyl acetate. Evaporation of the solvents afforded the aldehyde (6) [oil, 0.5 g. 70% by NMR]. The aldehyde (0.45 g) (6) in ethanol (50 ml) was added to dimethylamine (1.3 eq). To this solution was added $NaBH_4$ (1.1 eq). The reaction mixture was stirred for 4 h and the treated with 1 N HCl at 0° C. After removal of the solvents, the residue was dissolved in water and washed with ethyl ether. The aqueous layer was concentrated under reduced pressure to afford compound (7) [0.32 g, 63% by NMR]. The amine (7) (0.3 g) in DMF (10 ml) was treated with MeI (1 ml, excess) overnight. The solvent was removed under reduced pressure to give compound (8) which was converted to analog (3) in a similar manner as analog (1) [semisolid, 85% by NMR].

Figure 3C:
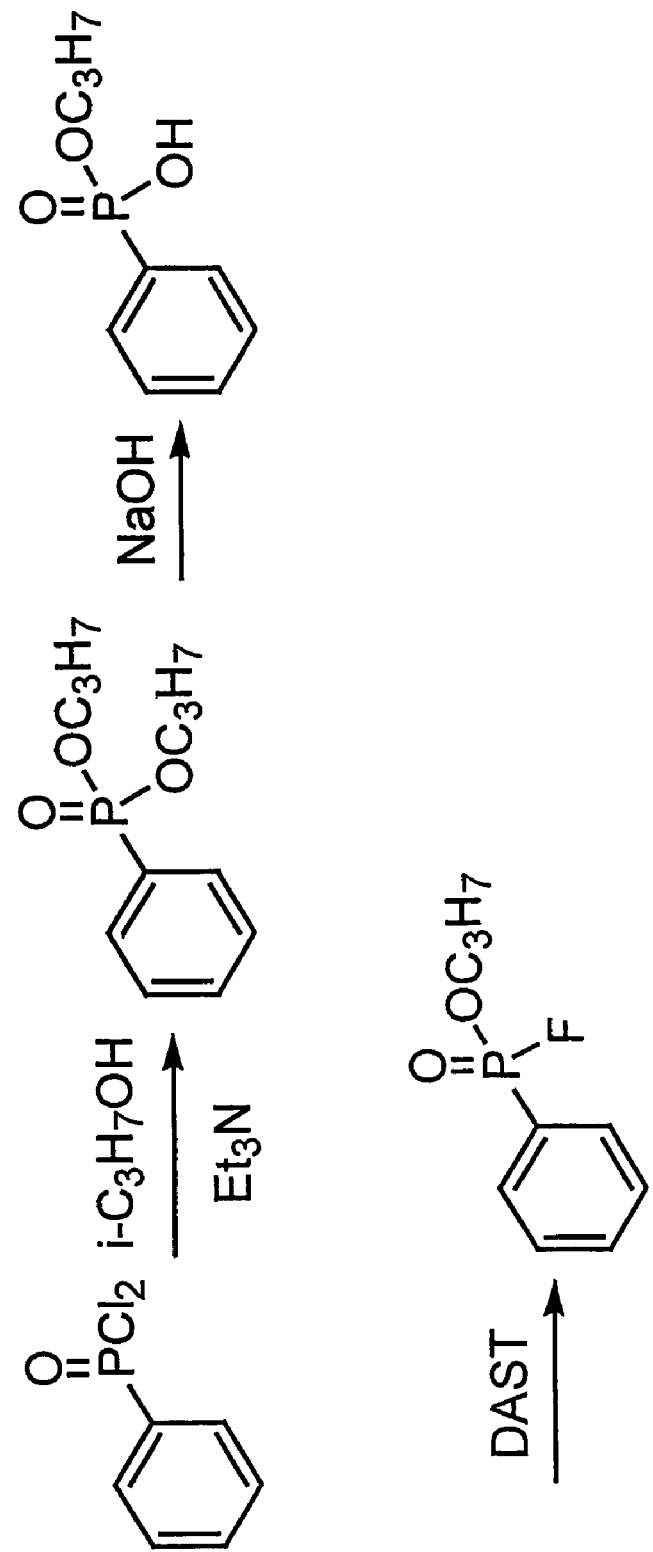
FIG. 3C: Synthesis of analog (4). Treatment of phenylphosphonic dichloride with excess isopropanol in the presence of triethylamine afforded the diisopropyl phenylphosphonate which was subjected to basic hydrolysis with NaOH to generate the monoester (isopropyl phenylphosphonic acid). The nerve gas analog (4) was generated by treatment with DAST in a manner similar to analog (1).

Synthesis of analog (4): Analog (4) was synthesized by the route outlined in scheme 3, FIG. 3C. Treatment of phenylphosphonic dichloride with excess isopropanol in the presence of triethylamine afforded the diisopropyl phenylphosphonate which was subjected to basic hydrolysis with NaOH to generate the monoester (isopropyl Phenylphosphonic acid). The nerve gas analog (4) was generated by treatment with DAST in a manner similar to analog (1).

Solution-phase Reaction of Peptides with Sarin Analogs 1 mmol of purified peptide was incubated with one of the nerve agent analogs (1.2 mmol) in PBS at room temperature for 2-3 hr. The formation of reaction product was monitored by HPLC ($C_{18}$ analytic column, gradient eluting with 100% $H_2O$—70% MeCN for 1 h) and confirmed by mass spectrophotometry.

Results and Discussion

In order to obtain catalytic peptides with the desired reactivity, libraries consisting of peptides containing a nucleophilic moiety were conceived which would react with the phosphonate moiety of organophosphorus-based agents to form a peptide phosphoester.

Initial work was done using hexapeptide libraries consisting of a serine at a fixed position [$x_1, x_2, \ldots x_6$] and any amino acid at each of the remaining five positions. In one example, the hydroxyl moiety of serine serves as the nucleophile which reacts with the phosphonate of the agent to form a peptide-phosphoester, effectively blocking the ability of the agent to react with cellular proteins and thus neutralizing it.

Each of the six hexapeptide libraries consists of at least 3.2 million peptides comprised of a random amino acid at each of five positions and a serine at a fixed position (given by probability $20^5=3.2\times10^6$). For example, Library 1 consists of at least 3.2 million peptides, each having a serine in position one ($x_1$) and any amino acid in each of the remaining five positions. In practice, each peptide was represented by approximately 6 copies in the library. Initially, three libraries were synthesized containing a fixed serine at either $x_1$, $x_2$, or $x_3$, respectively.

In order to identify peptides with the desired reactivity, labeled analogs of the nerve gas sarin were synthesized. Labeled butylcholinesterase (BuChE) coupled to the same solid support as the library (in this case Tental Gel™) was used as a positive control to identify peptides with suitable reaction kinetics.

Although radiolabeled analogs are preferable because they minimize interference due to steric hinderance, such analogs of nerve agents present unacceptable hazards. Therefore, fluorescent sarin analogs were generated using each of rhodamine, fluorescein, cascade blue, dansyl cadaerine and disperse red as labels. Preliminary experiments using native beads as negative controls demonstrated that rhodamine-conjugated sarin analog (1) produced the optimal signal to noise ratio.

Library screening was performed with analog (1) and fluorescent beads were selected. Initially, beads demonstrating the highest fluorescence intensity were manually selected under the microscope. However, this technique could easily be optimized for selection using high-throughput methods such as flow cytometry (for libraries coupled to beads), plate readers (for libraries adsorbed onto microtiter plates) or microarray scanners (for libraries on microchips).

23 of the manually selected fluorescent beads were chosen for sequencing and a further subset of ten of the resulting peptides was chosen for resynthesis and further study. These ten peptides had the following sequence: YKDNSY (SEQ ID NO:1), YKDISY (SEQ ID NO:2), DNFKSY (SEQ ID NO:3), ANKYSY (SEQ ID NO:4), YYCDSY (SEQ ID NO:5), YHYYSY (SEQ ID NO:6), ANYYSY (SEQ ID NO:7), YEYQSY (SEQ ID NO:8), LIFASY (SEQ ID NO:9), YKEFSY (SEQ ID NO:10), and CAYCSY (SEQ ID NO:11)

Purified peptides identified in the initial screen were further tested for reactivity against sarin analog (2), which lacked the fluorescent tag. Using HPLC to monitor the reaction, one peptide was found to react with analog (2), demonstrated by the loss of its characteristic peak and the emergence of three new chromatographic peaks. YKDNSY disappeared at retention time 17 min, and the 3 new peaks appeared at 23, 25 and 29 min. $^1$H NMR analysis demonstrated that the peaks at 4.9 ppm (H for $Me_2CHP(O)F$) shifted to 4.5 ppm (H for $Me_2CHP(O)O$), indicating formation of a phosphoester with the sarin analog. Diastereomers likely account for two of the products.

REFERENCES

Cheng, T. C. et al., Cloning and expression of a gene encoding a bacterial enzyme for decontamination of organophosphorus nerve agents and nucleotide sequence of the enzyme. *Appl. Env. Microbiol.* 62, 1636-1641 (1996)

Doctor, B. P., Richard K., et al., Immobilized enzymes: Nerve agent detoxifiers. *Proceedings of the ERDEC Scientific Conference on Chemical and Biological Defense Research, Aberdeen Proving Ground, MD, United States*, Nov. 17-20, 1998, p. 559-566 (1999).

Gill, I., and Ballesteros, A., Degradation of organophosphorous nerve agents by enzyme-polymer nanocomposites: efficient biocatalytic materials for personal protection and large-scale detoxification. *Biotech. Bioeng.* 70(4), 400-410 (2000).

LeJeune, K. E., Wild, J. R., Russell, A. J., Nerve agents degraded by enzymic foams. *Nature* 395(6697), 27-28 (1998).

Lejeune, K. E., Dravis, B. C., Yang, F., Retro, A. D., Doctor, B. P., Russell, A. J., Fighting nerve agent chemical weapons with enzyme technology. *Ann. N.Y. Acad. Sci.* 864, 153-170 (1998).

Lejeune, K. E. and Russell, A. J., Biocatalytic nerve agent detoxification in fire fighting foams. *Biotechnol. Bioeng.* 62(6), 659-665 (1999).

What is claimed is:

1. A peptide which forms a phosphorus-based ester with an organophosphorus agent, wherein said peptide is selected from the group consisting of SEQ ID NOS: 1-11.

2. The peptide of claim 1, wherein the is SEQ ID NO: 1.

3. The peptide of claim 2, wherein the peptide has a length of six amino acid residues.

4. The peptide of claim 1, wherein the molecular weight of the peptide is less than 1500 daltons.

5. A composition of matter comprising the peptide of claim 1 and a carrier.

6. The composition of claim 5, wherein the carrier is a foam or an aerosol.

7. An article of manufacture comprising a peptide of claim 1, wherein said peptide is affixed to a solid substrate.

* * * * *

SEQUENCE LISTING

```
<160> NUMBER OF SEQ ID NOS: 11

<210> SEQ ID NO 1
<211> LENGTH: 6
<212> TYPE: PRT
<213> ORGANISM: Artificial
<220> FEATURE:
<223> OTHER INFORMATION: synthetic peptide

<400> SEQUENCE: 1

Tyr Lys Asp Asn Ser Tyr
1               5

<210> SEQ ID NO 2
<211> LENGTH: 6
<212> TYPE: PRT
<213> ORGANISM: Artificial
<220> FEATURE:
<223> OTHER INFORMATION: synthetic peptide

<400> SEQUENCE: 2

Tyr Lys Asp Ile Ser Tyr
1               5

<210> SEQ ID NO 3
<211> LENGTH: 6
<212> TYPE: PRT
<213> ORGANISM: Artificial
<220> FEATURE:
<223> OTHER INFORMATION: synthetic peptide

<400> SEQUENCE: 3

Asp Asn Phe Lys Ser Tyr
1               5

<210> SEQ ID NO 4
<211> LENGTH: 6
<212> TYPE: PRT
<213> ORGANISM: Artificial
```

```
<220> FEATURE:
<223> OTHER INFORMATION: synthetic peptide

<400> SEQUENCE: 4

Ala Asn Lys Tyr Ser Tyr
1               5

<210> SEQ ID NO 5
<211> LENGTH: 6
<212> TYPE: PRT
<213> ORGANISM: Artificial
<220> FEATURE:
<223> OTHER INFORMATION: synthetic peptide

<400> SEQUENCE: 5

Tyr Tyr Cys Asp Ser Tyr
1               5

<210> SEQ ID NO 6
<211> LENGTH: 6
<212> TYPE: PRT
<213> ORGANISM: Artificial
<220> FEATURE:
<223> OTHER INFORMATION: synthetic peptide

<400> SEQUENCE: 6

Tyr His Tyr Tyr Ser Tyr
1               5

<210> SEQ ID NO 7
<211> LENGTH: 6
<212> TYPE: PRT
<213> ORGANISM: Artificial
<220> FEATURE:
<223> OTHER INFORMATION: synthetic peptide

<400> SEQUENCE: 7

Ala Asn Tyr Tyr Ser Tyr
1               5

<210> SEQ ID NO 8
<211> LENGTH: 6
<212> TYPE: PRT
<213> ORGANISM: Artificial
<220> FEATURE:
<223> OTHER INFORMATION: synthetic peptide

<400> SEQUENCE: 8

Tyr Glu Tyr Gln Ser Tyr
1               5

<210> SEQ ID NO 9
<211> LENGTH: 6
<212> TYPE: PRT
<213> ORGANISM: Artificial
<220> FEATURE:
<223> OTHER INFORMATION: synthetic peptide

<400> SEQUENCE: 9

Leu Ile Phe Ala Ser Tyr
1               5

<210> SEQ ID NO 10
<211> LENGTH: 6
<212> TYPE: PRT
<213> ORGANISM: Artificial
```

-continued

```
<220> FEATURE:
<223> OTHER INFORMATION: synthetic peptide

<400> SEQUENCE: 10

Tyr Lys Glu Phe Ser Tyr
1               5

<210> SEQ ID NO 11
<211> LENGTH: 6
<212> TYPE: PRT
<213> ORGANISM: Artificial
<220> FEATURE:
<223> OTHER INFORMATION: synthetic peptide

<400> SEQUENCE: 11

Cys Ala Tyr Cys Ser Tyr
1               5
```